United States Patent [19]
Ekstrom et al.

[11] Patent Number: 6,016,685
[45] Date of Patent: Jan. 25, 2000

[54] APPARATUS FOR MEASURING THE COEFFICIENT OF FRICTION OF A GOLF BALL

[75] Inventors: Erik A. Ekstrom, Wilkes-Barre; Stanley H. Johnson, Bethlehem, both of Pa.

[73] Assignee: United States Golf Associatino, Far Hills, N.J.

[21] Appl. No.: 09/041,585

[22] Filed: Mar. 12, 1998

[51] Int. Cl.[7] .................................................. G01N 19/02
[52] U.S. Cl. ...................................... 73/9; 73/859
[58] Field of Search ................... 73/9, 859, 860, 73/818, 819

[56] References Cited

U.S. PATENT DOCUMENTS

| | | | |
|---|---|---|---|
| 1,825,387 | 9/1931 | Esnault-Pelterie | 73/9 X |
| 3,665,757 | 5/1972 | Hoay | 73/818 |
| 4,498,329 | 2/1985 | Bloomer, II et al. | 73/9 |
| 4,627,293 | 12/1986 | Bechtel | 73/859 X |

FOREIGN PATENT DOCUMENTS 285239  11/1990  Japan .

*Primary Examiner*—Thomas P. Noland
*Attorney, Agent, or Firm*—McAulay Nissen Goldberg Kiel & Hand, LLP

[57] ABSTRACT

The testing apparatus serves to measure the coefficient of friction of a golf ball. The apparatus has a base with a pair of flexure arms which carry inserts between which a golf ball may be pushed under a force in order to flex the flexure arms outwardly. Strain gauges record the flexing of the flexure arms in order to determine the force perpendicular to an insert. A load cell is employed to determine the amount of pushing force on the golf ball in order to determine a force parallel to the surface of the insert. The ratio of the two forces obtained serves as the coefficient of friction of a golf ball.

5 Claims, 3 Drawing Sheets

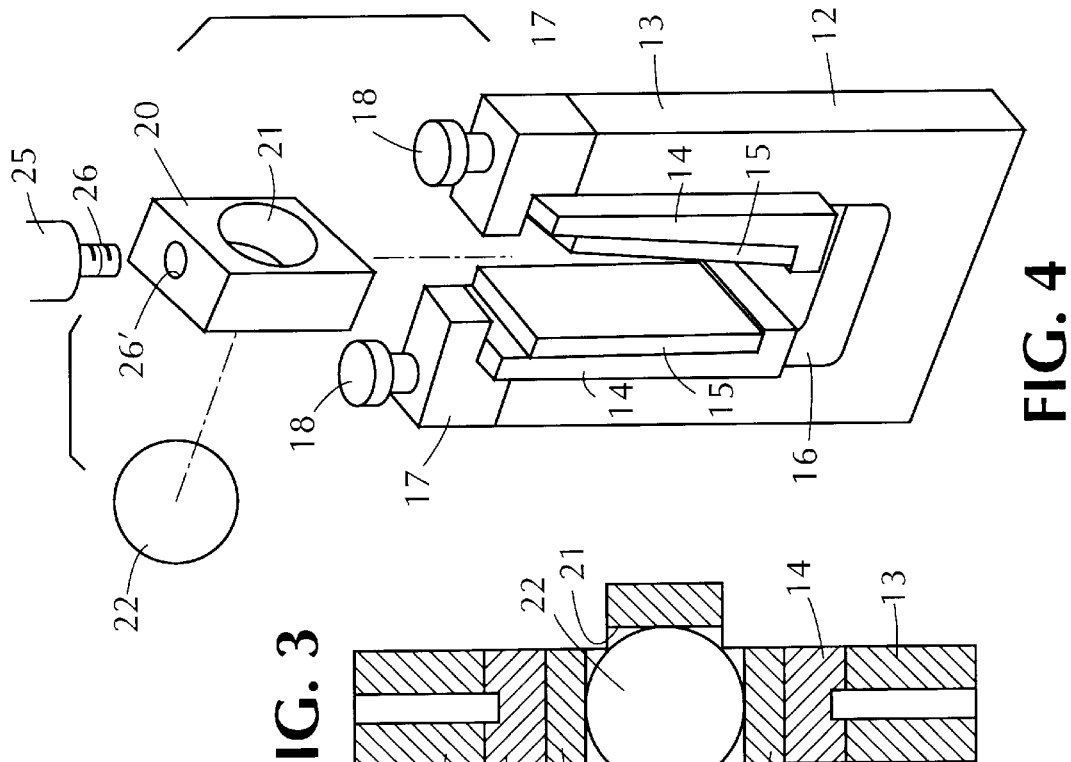
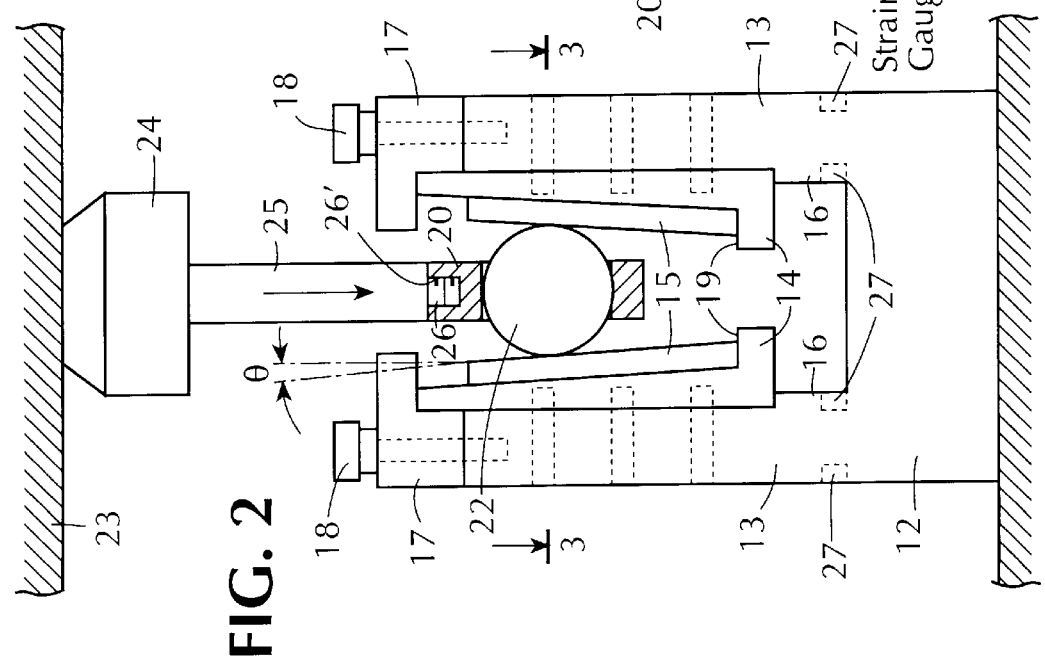

APPARATUS FOR MEASURING THE COEFFICIENT OF FRICTION OF A GOLF BALL

BACKGROUND OF THE INVENTION

This invention relates to an apparatus for measuring the coefficient of friction of a golf ball.

As is known, the coefficient of friction of a golf ball has a direct effect on the amount of spin imparted to a golf ball when hit by a golf club. That is to say, the measurement of friction between the golf club and the golf ball is important in assessing the spin characteristics of a golf ball, particularly for a high lofted iron. Traditionally, it has been accepted that the back spin imparted to a golf ball is that which enables a player to stop the ball on a green. However, the main function of a back spin is not to stop the ball on a green but to provide aerodynamic lift that prolongs flight time.

As described by Gobush W., "Spin And The Inner Workings Of A Golf Ball", Golf The Scientific Way edited by A. J. Cochran, Aston Publishing Group, 1995, pages 141–145, there are two components of force which act on a golf ball during impact with an iron. One force is at a right angle to the club face and is represented as the vector $F_N$ and the other force is parallel to the club face or tangential to the golf ball and is designated as the vector $F_T$. The normal force $F_N$ projects the ball forward while the tangential force $F_T$ applies spin. The ratio of these two forces represents the coefficient of friction of the ball on the club face.

In the past, various types of techniques have been used to obtain a measurement of the coefficient of friction of a golf club face. One technique employs an air cannon which is used to eject golf balls at a force transducer surface and a camera system which is used to capture the golf ball at positions before and after impact with the force transducer. However, such a technique requires relatively cumbersome types of structures and requires photographic analysis of the golf ball.

SUMMARY OF THE INVENTION

Accordingly, it is an object of the invention to provide a relatively simple apparatus for measuring the coefficient of friction of a golf ball.

It is another object of the invention to be able to measure the coefficient of friction of a golf ball in a static apparatus.

Briefly, the invention provides a testing apparatus for measuring the coefficient of friction of a golf ball which includes a base having a pair of flexure arms disposed in opposed parallel relation to each other, a pair of wedges, each of which is mounted in abutting relation to a respective flexure arm to define a gap of decreasing width with the other wedge and a golf ball holder for receiving a golf ball. In addition, the apparatus includes a means for moving the golf ball holder into and between the wedges in order to abut a golf ball in the holder against the two wedges and to flex the two flexure arms outwardly of each other under a pushing force imposed on the ball holder.

The testing apparatus also employs a plurality of strain gauges which are connected to the two flexure arms in order to sense an outward flexing of each flexure arm as well as a load cell connected with the means for moving the ball holder for measuring the pushing force imposed on the holder to move the ball between the two wedges.

Still further, the testing apparatus includes a processing unit which is connected to the strain gauges to receive signals therefrom indicative of the flexing of the two flexure arms in order to determine a corresponding force ($F_N$) perpendicular to the wedges from the signals. The processing unit is also connected to the load cell to receive signals therefrom indicative of the pushing force on the ball holder and to determine a corresponding force ($F_T$) parallel to a surface of each wedge from the received signal.

The processing unit is also programmed to emit an output signal indicative of the ratio of the force parallel to a surface of the wedges and the force perpendicular to the wedges as the coefficient of sliding friction of the ball in the holder on the wedges.

In order to be able to test a golf ball against various types of surfaces, the apparatus employs a pair of inserts, each of which is removably mounted on a respective one of the wedges in order to contact a golf ball in the golf ball holder. For example, each insert may be made of steel with a smooth or rough face. Alternatively, the insert may be made of any other suitable material which corresponds with a material used to make a golf club face, particularly for a lofted iron.

The testing apparatus may be incorporated in a conventional compression/tension machine and coordinated with a movable beam.

In use, the ball holder is secured to the movable beam of the compression/tension machine so as to be moved between the inserts mounted on the flexure arms of the testing apparatus. In this respect, a load cell is placed between the beam and the ball holder in order to emit signals corresponding to the force imposed on the golf ball in the holder in order to move the golf ball between the two inserts.

As the golf ball holder moves through the gap defined by the two inserts of the testing apparatus, the two arms of the base are flexed outwardly. The amount of flexing or strain in each flexure arm is sensed by the plurality of strain gauges attached to each flexure arm. Since each strain gauge is mounted at a predetermined distance from the base of a flexure arm, the moment of the flexure arm can be calculated by the processing unit.

The processing unit is programmed, using a suitable computer program, in order to convert the signals from the strain gauges and the signal from the load cell to a coefficient of sliding friction. In this respect, the signal from the load cell is indicative of a force parallel to a surface of each wedge. That is to say, the force on the ball produces a vector force perpendicular to each insert and a force vector parallel to the insert.

The strain gauges determine the amount of flexing or strain caused by the movement of the golf ball between the two inserts. The processing unit is programmed to determine the force perpendicular to each insert causing the flexing of the flexure arm.

By dividing the force which is parallel to the face of the insert by the force normal or perpendicular to the face of the insert, the coefficient of friction of the golf ball is obtained.

BRIEF DESCRIPTION OF THE DRAWINGS

These and other objects and advantages of the invention will become more apparent from the following detailed description taken in conjunction with the accompanying drawings wherein:

FIG. 2 illustrates an enlarged view of the testing apparatus constructed in accordance with the invention;

FIG. 3 illustrates a cross sectional view taken on line 3—3 of FIG. 2;

FIG. 4 illustrates an exploded view of the testing apparatus of FIG. 2; and

DETAILED DESCRIPTION OF THE INVENTION

Figure 1:
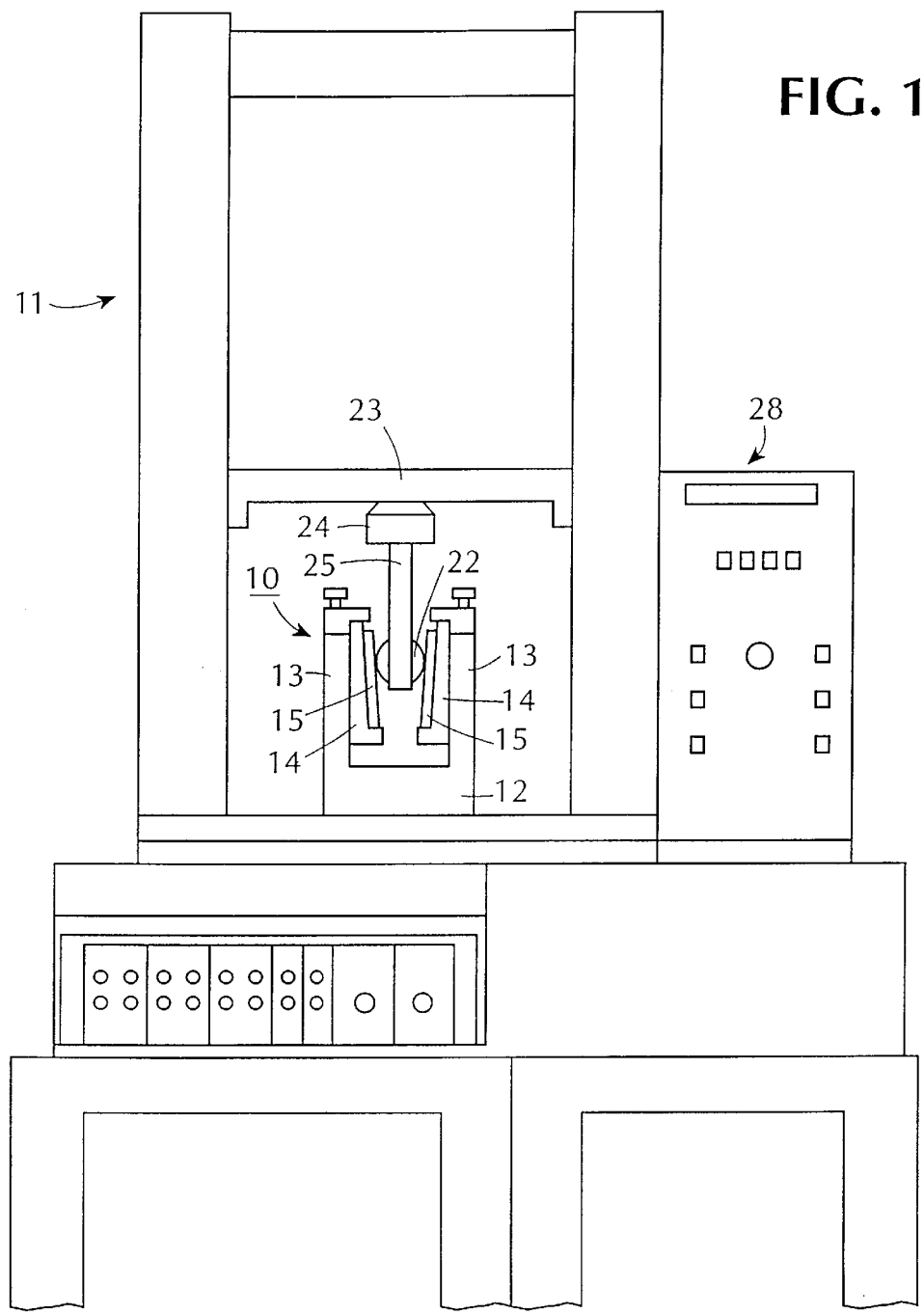
FIG. 1 illustrates a front view of a compression/tension machine employing a testing apparatus in accordance with the invention.

Referring to FIG. 1, the testing apparatus 10 is incorporated in a conventional compression/tension machine 11.

Referring to FIG. 2, the testing apparatus 10 includes a base 12 having a pair of upstanding flexure arms 13 disposed in parallel relation to each other. This base 12 may be made of any suitable material such as stainless steel.

In addition, the testing apparatus 10 includes a pair of wedges 14 each of which is mounted in abutting relation to a respective flexure arm 13 in order to define a gap of decreasing width with the other wedge 14. In the illustrated embodiment, each wedge 14 has a flat surface facing the gap which is at an angle θ to a vertical plane. A pair of inserts 15 are also provided, one on each wedge 14. These inserts 15 are removably mounted on the wedges 14 and are made of material corresponding to materials used for golf club faces. For example, each insert 15 may be made of steel with a smooth or a rough surface facing the gap and disposed at the angle θ to a vertical plane.

As illustrated in FIG. 2, each flexure arm 13 has a shoulder 16 at the lower end against which a wedge 14 is abutted. In addition, a bracket 17 is secured to the end of each flexure arm 13 by means of a threaded nut or bolt 18 in order to fixedly secure a respective wedge 14 in place.

As indicated in FIG. 2, each wedge 14 has a small shoulder 19 at a lower end, as viewed, upon which an insert 15 rests. Any suitable means may be provided to hold an insert 15 on a wedge 14. For example, each wedge 14 may be provided with a series of holes while each insert 15 has a plurality of pins (not shown) on a back surface to be received in the holes of a wedge 14. Further, as indicated in FIG. 2, each bracket 17 serves not only to hold a wedge 14 within the base 12 but also serves to hold an insert 15 against the respective wedge 14.

Referring to FIGS. 2 and 4, the testing apparatus 10 also employs a golf ball holder 20 for receiving a golf ball. As indicated, the holder 20 is in the form of a square nut with a central bore 21 within which the golf ball 22 may be positioned. In this respect, the golf ball 22 is free to rotate within the holder 20.

A means is also provided for moving the ball holder 20 into and between the wedges 14 in order to abut the golf ball 22 in the holder 20 against the wedges 14 and particularly against the inserts 15 in order to flex the flexure arms 13 of the base 12 outwardly of each other under a pushing force imposed on the ball holder 20. In this respect, as indicated in FIG. 1, the compression/tension machine 11 is of a conventional structure and has a movable beam 23 which can be moved relative to the testing apparatus 10. As indicated in FIG. 1, the beam is moved vertically.

A load cell 24 is also provided between the beam 23 and the ball holder 20 in order to emit signals corresponding to the pushing force imposed upon the ball 22 in order to move the ball 22 through the decreasing gap defined between the inserts 15. As indicated in FIG. 2, the load cell 24 may be connected to the ball holder 20 via a shaft 25 which has a threaded stem 26 threadably mounted in a threaded bore 26' of the holder 20.

Referring to FIG. 1, the testing apparatus 10 also includes a plurality of strain gauges 27 which are located on the inside and outside of each flexure arm 13 of the base 12 near the lower end of each arm 13. Each strain gauge 27 serves to sense an outward flexing of the respective flexure arm 13 and emits a signal corresponding thereto.

As indicated in FIG. 1, the testing apparatus 10 employs a processing unit 28 which is mounted on the frame 29 of the compression/tension machine 11. This processing unit 28 is connected to the strain gauges 27 in order to receive signals therefrom indicative of the flexing of the flexure arms 13. In addition, the processing unit 28 is programmed to receive the signals and to determine a corresponding force ($F_N$) perpendicular to the inserts 15 from the signals.

The processing unit 28 is also connected to the load cell 24 to receive signals therefrom indicative of the pushing force on the ball holder 20 and serves to determine a corresponding force ($F_T$) parallel to a surface of each insert 15 from the signal received from the load cell 24.

Still further, the processing unit 28 is programmed to emit an output signal indicative of the ratio of the force parallel to a surface of an insert 15 relative to the force perpendicular to the insert 15 as the coefficient of sliding friction of the ball in the holder on the insert In use, a golf ball 22 is mounted in the ball holder 20. Thereafter, the ball holder 20 is moved between the two inserts 15 of the testing apparatus to flex the flexure arms 13 of the tester apparatus outwardly. During this time, signals are received by the processing unit 28 from the load cell 24 and the strain gauges 27 in order to provide a dynamic record of the forces over time. After a suitable point has been reached, the forces $F_N$ and $F_T$ are calculated and the ratio of these forces to each other is determined as the coefficient of friction of the golf ball.

Figure 5:
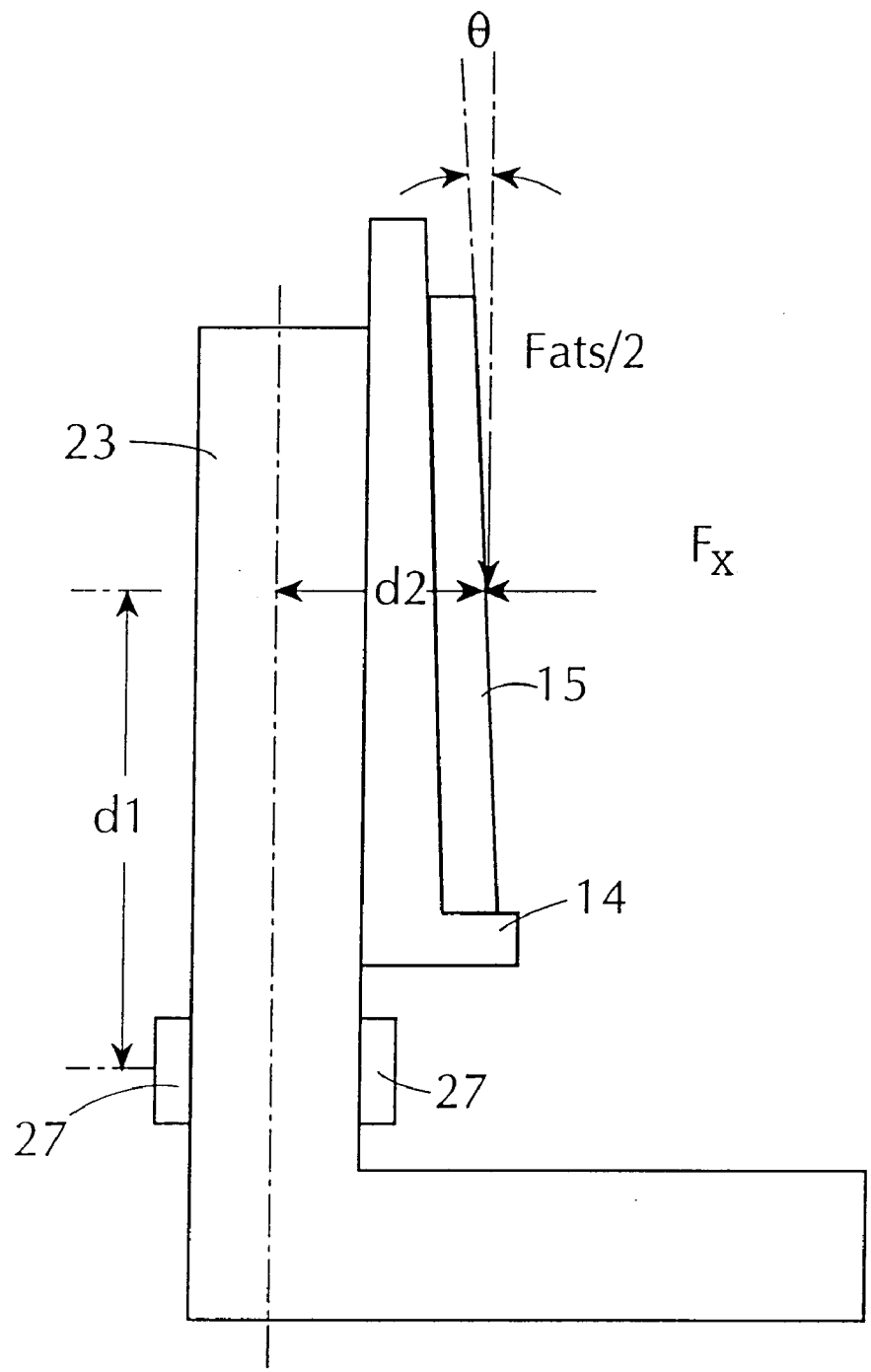
FIG. 5 illustrates the forces imposed on a flexure arm of the testing apparatus.

Referring to FIG. 5, in order to obtain the forces $F_N$ and $F_T$, use is made of the following formulae:

$$F_T = 1/2 F_{ATS} \cos\theta - F_X \sin\theta$$

$$F_N = F_X \cos\theta + 1/2 F_{ATS} \sin\theta$$

$$\mu = \frac{(F_{ATS}\cos\theta - 2F_X \sin\theta)}{(2F_X \cos\theta + F_{ATS}\sin\theta)}$$

Where:

θ is the angle of the surface of the insert 15 to the vertical.

$F_{ATS}$ is the force read from the load cell. (See FIG. 5)

$F_x$ is the force perpendicular to Fats.

For when the ball is being driven down into the plates:

$$F_X = \left(\varepsilon * \frac{EI}{y} + \frac{F_{ATS}}{2} * d_2\right) d_1$$

Where: $d_1$ is the vertical distance of the point at which the force $F_x$ is applied to the Center of the strain gauge 27;

$d_2$ is the horizontal distance of the point at which the force $F_{ATS}/2$ is applied to the center (centerline of the flexure arm 13;

y is the distance of the centroid of the flexure arm 13 to the outer surface of the flexure arm 13 and the outer strain gauge 27.

For when the ball is pulled out of the plates:

$$F_X = \left(\varepsilon * \frac{EI}{y} + \frac{F_{ATS}}{2} * d_2\right) d_1$$

Where $\varepsilon$ is the strain read from the strain gauges and EI/y is a constant determined from calibrating the strain gauge 27.

In this respect, the testing apparatus 10 is calibrated by being placed on one side so that 19, the flexure aims 13 are horizontal. A known force is then applied to the top surface of the upper flexure arm 13 so as to deflect the arm downwardly. Knowing the distance (D) from the point of application of the force (F) to the topmost strain gauge 27 and knowing the strain ($\varepsilon$), a constant may be developed for the expression EI/Y. The following formulas are used for this calibration:

$$\sigma = \frac{My}{I} = \varepsilon E; \quad M = Fd;$$

$$F = \frac{M}{d} = \frac{\varepsilon EI}{yd}$$

The forces $F_N$ and $F_T$ are determined at every point that the data is read. The final coefficient of friction $\mu$ that is reported is the average of all the coefficients of friction $\mu$ determined during testing. The coefficient of friction should be a constant no matter what loads are applied. The experimental results obtained demonstrate that this is true.

A preferred minimum travel distance for a golf ball between the two inserts 15 is from 1 inch to 1.5 inches. These minimum travel distances have been found to provide a suitable average of the coefficient of friction so that a few outlying data points will not bias the average value.

The golf balls which are tested may have any suitable cover materials such as the balata, Surlyn® or any other suitable material used for golf balls.

The invention thus provides a relatively simple apparatus for determining the coefficient of friction of a golf ball. In particular, the testing apparatus is of a static nature and does not require any photographic analysis or any air cannons for propelling a ball against an insert Further, the apparatus allows the use of different types of inserts with different types of surfaces in order to obtain measurements for the coefficient of friction of a given golf ball.

What is claimed is:

1. A testing apparatus for measuring the coefficient of friction of a golf ball, said apparatus comprising a base having a pair of flexure arms disposed in opposed parallel relation to each other;

a pair of wedges, each wedge being mounted in abutting relation to a respective flexure arm and defining a gap of decreasing width with the other wedge of said pair of wedges;

a golf ball holder for receiving a golf ball;

means for moving said ball holder into between said wedges to abut a golf ball in said holder against said wedges and to flex said flexure arms outwardly of each other under a pushing force imposed on said ball holder;

a plurality of strain gauges connected to said flexure arms to sense an outward flexing of each said flexure arm; and a load cell connected with said means for moving said ball holder for measuring said pushing force imposed on said holder.

2. An apparatus as set forth in claim 1 further comprising a processing unit connected to said strain gauges to receive signals therefrom indicative of the flexing of said flexure arms and to determine a corresponding force (F) perpendicular to said wedges from said signals, said processing unit being connected to said load cell to receive signals therefrom indicative of said pushing force and to determine a corresponding force (F) parallel to said surface of each said wedge from said signal, said processing unit emitting an output signal indicative of the ratio of said force parallel to a surface of said wedges relative to said force perpendicular to said wedges as the coefficient of sliding friction of the ball in said holder on said wedge.

3. An apparatus as set forth in claim 1 further comprising a pair of inserts, each insert being removably mounted on a respective one of said wedges to contact a golf ball in said holder.

4. An apparatus as set forth in claim 3 wherein each insert has a smooth surface facing the other of said inserts.

5. An apparatus as set forth in claim 3 wherein each insert is made of steel.

* * * * *

UNITED STATES PATENT AND TRADEMARK OFFICE
CERTIFICATE OF CORRECTION

PATENT NO. : 6,016,685
DATED : January 25, 2000
INVENTOR(S) : Erik A. Ekstrom and Stanley H. Johnson It is certified that error appears in the above-identified patent and that said Letters Patent is hereby corrected as shown below:

Column 5, line 10 change "19, the flexure aims 13" to -the flexure arms 13-

Signed and Sealed this

Fifth Day of December, 2000

Attest:

Attesting Officer

Q. TODD DICKINSON
Director of Patents and Trademarks